US012805515B2

(12) United States Patent
Tellkamp et al.

(10) Patent No.: US 12,805,515 B2
(45) Date of Patent: Nov. 24, 2026

(54) METHODS AND APPARATUS FOR PROVIDING BIOLOGICAL SAMPLES IN A VITRIFIED STATE FOR STATIC AND TIME-RESOLVED STRUCTURAL INVESTIGATIONS USING ELECTRON OR X-RAY SOURCES

(71) Applicant: Max-Planck-Gesellschaft zur Förderung der Wissenschaften e. V., Munich (DE)

(72) Inventors: Friedjof Tellkamp, Hamburg (DE); Eike-Christian Schulz, Hamburg (DE); Hendrik Schikora, Hamburg (DE); Pedram Mehrabi, Hamburg (DE); Martin Kollewe, Hamburg (DE)

(73) Assignee: Max-Planck-Gesellschaft zur Förderung der Wissenschaften E. V., München (CH)

( * ) Notice: Subject to any disclaimer, the term of this patent is extended or adjusted under 35 U.S.C. 154(b) by 740 days.

(21) Appl. No.: 18/119,620

(22) Filed: Mar. 9, 2023

(65) Prior Publication Data

US 2023/0284610 A1 Sep. 14, 2023

(30) Foreign Application Priority Data

Mar. 10, 2022 (EP) .................................... 22161384

(51) Int. Cl.
*A01N 1/10* (2025.01)
*A01N 1/142* (2025.01)
*A61B 10/00* (2006.01)

(52) U.S. Cl.
CPC ............ *A01N 1/10* (2025.01); *A61B 10/0096* (2013.01); *A01N 1/142* (2025.01)

(58) Field of Classification Search
CPC ...... A01N 1/10; A01N 1/142; A61B 10/0096; G01N 23/20025; G01N 35/1002;
(Continued)

(56) References Cited

U.S. PATENT DOCUMENTS

| | | | |
|---|---|---|---|
| 4,563,883 A | 1/1986 | Sitte | |
| 2018/0209881 A1 | 7/2018 | Arnold et al. | |
| 2022/0381656 A1* | 12/2022 | Bormans | G01N 1/30 |

FOREIGN PATENT DOCUMENTS

| | | |
|---|---|---|
| EP | 2381236 | 10/2011 |
| WO | 03050598 | 6/2003 |

OTHER PUBLICATIONS

European Search Report from corresponding European Application No. 22161384.7 dated Sep. 9, 2022.

(Continued)

*Primary Examiner* — John McGuirk
(74) *Attorney, Agent, or Firm* — Grogan, Tuccillo & Vanderleeden, LLP

(57) ABSTRACT

The invention relates to a method for vitrifying a biological sample. The method includes positioning a sample holder with the biological sample by a transfer device in a starting position. The sample holder has a base and a pin projecting from the base along a holder axis. Further, the biological sample is attached to the pin distant from the base. The method further comprises adding a liquid to the biological sample in the starting position by a liquid dispenser. Further, the method comprises moving the sample holder with the biological sample by the transfer device along a predetermined transfer path from the starting position to a release position, wherein the biological sample in the release position is arranged in or adjacent to a liquefied gas. It is provided that the transfer path is inclined with respect to the holder axis or runs along a circular arc. Furthermore, the (Continued)

Figure 1:
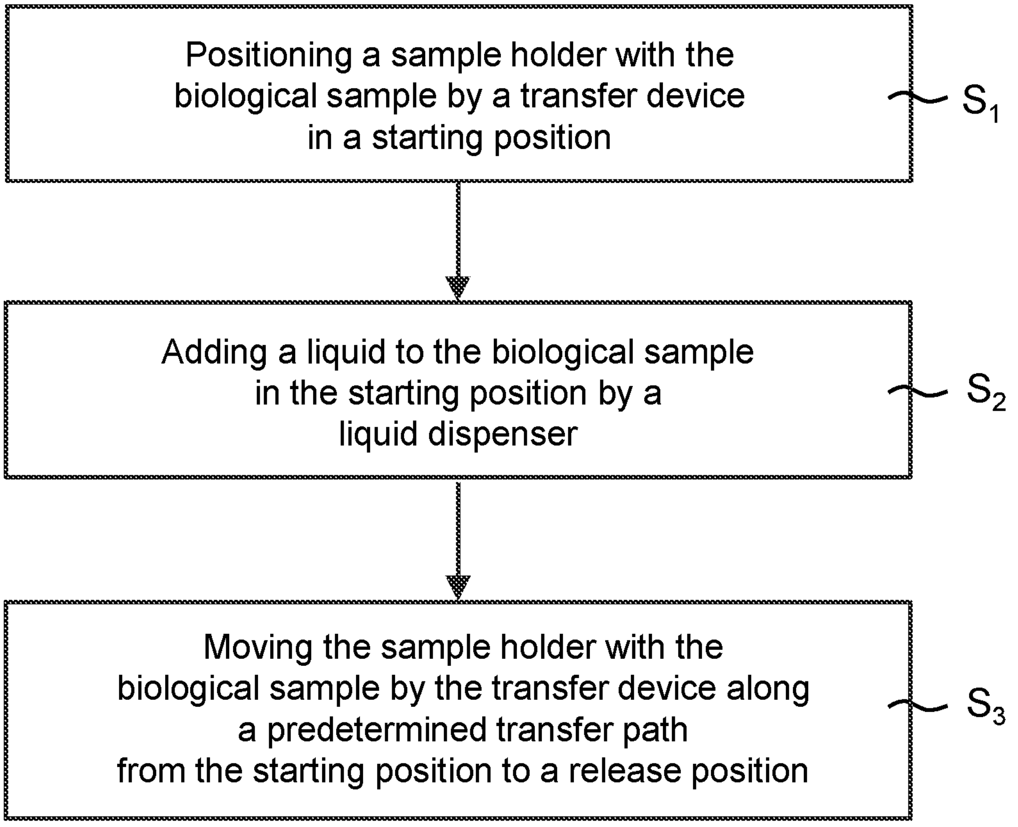

invention relates to a vitrification apparatus which is configured to perform the method.

19 Claims, 6 Drawing Sheets

(58) Field of Classification Search
CPC ........... G01N 2035/0429; G01N 35/04; G01N 2035/00445; G01N 2035/1034; G01N 2223/203; G01N 1/42
See application file for complete search history.

(56) References Cited

OTHER PUBLICATIONS

F. Cipriani; "Spine Sample Holder & Vial Specifications-L-R05"; The Spine Committee; Apr. 15, 2014.
P. Mehrabi et al.; "Liquid Application Method for time-resolved analyses by serial synchotron crystallogrpahy"; Nature Methods; Oct. 2019; pp. 979-982; vol. 16; Nature Portfolio; New York, NY.
P. Mehrabi et al.; "Time-resolved crystallography reveals allosteric communication aligned with molecular breathing"; Science; Sep. 13, 2019; pp. 1167-1170; American Association for the Advancement of Science; Washington, DC.
P. Mehrabi et al.; "The HARE chip for efficient time-resolved serial synchrotron crystallography"; "Journal of Synchrotron Radiation"; Jan. 20, 2020; pp. 360-370; Wiley-Blackwell on behalf of the International Union of Crystallography; Chester, UK.
E. Schulz et al.; "The hit-and-return system enables efficient time-resolved serial synchrotron crystallography"; Nature Methods; Nov. 2018; pp. 901-904; vol. 15; Nature Portfolio; New York, NY.

* cited by examiner

METHODS AND APPARATUS FOR PROVIDING BIOLOGICAL SAMPLES IN A VITRIFIED STATE FOR STATIC AND TIME-RESOLVED STRUCTURAL INVESTIGATIONS USING ELECTRON OR X-RAY SOURCES

CROSS-REFERENCE TO RELATED APPLICATION

This application claims priority to European Patent Application No. EP 22161384.7 filed Mar. 10, 2022, all of which is hereby incorporated by reference in its entirety.

TECHNICAL FIELD

The invention relates to methods for vitrifying biological samples. Furthermore, the invention relates to a vitrification apparatus, which is configured to perform one of these methods. Possible applications of the invention include the preparation of biological samples (e.g., protein crystals) in a vitrified state for static and/or time-resolved structural investigations using electron or X-ray sources.

RELATED ART

In the present application, reference is made to the following documents, which clarify the technical background of the invention:

[1] SPINE SAMPLE HOLDER & VIAL SPECIFICATIONS-L-R05 (Apr. 15, 2014); P. Mehrabi et al, "Liquid application method for time-resolved analyses by serial synchrotron crystallography", Nat. Methods 16, 979-982 (2019);

[3] P. Mehrabi et al, "Time-resolved crystallography reveals allosteric communication aligned with molecular breathing", Science 365, 1167-1170 (2019);

[4] E. C. Schulz et al, "The hit-and-return system enables efficient time-resolved serial synchrotron crystallography", Nat. Methods 15, 901-904 (2018);

[5] P. Mehrabi et al, "The HARE chip for efficient time-resolved serial synchrotron crystallography", J. Synchrotron Rad. 27, 360-370 (2020);

Time-resolved investigations at synchrotron radiation sources or electron microscopes are important methods to determine the structure of biological samples and especially their dynamics. The method mainly used for this purpose is the diffraction of synchrotron radiation or coherent electrons, from whose diffraction images the structure may be reconstructed. For this purpose, the biological samples, primarily proteins, must be in crystalline form and placed in the beam, e.g., of synchrotron radiation.

An established method for the investigation of protein crystals at synchrotron radiation sources is the mounting of single or multiple microscopic crystals (e.g. with typical cross-sectional dimensions in the range of 10 μm to 100 μm) on a special type of sample holder. These sample holders, defined by the SPINE standard [1] and sold by various manufacturers, have a cap that serves as a holder for a pin projecting from the cap. One or more protein crystals to be examined are attached to the free end of the pin (e.g. by means of a mesh or a microscopic loop) and measured in the beam.

Since protein crystals mainly consist of water, they must be protected from drying out between their preparation and the diffraction examination. This is usually done by freezing or vitrifying, i.e. by very rapid cooling (shock freezing) of the crystals (e.g. in liquid nitrogen or ethane). Samples frozen in this way can be prepared independently of the availability of a measurement at a synchrotron radiation source in terms of time and space. It is common practice to store several sample holders loaded with crystals in a designated storage device and/or to ship them to a synchrotron radiation source. Many synchrotron radiation sources worldwide use standardized geometries for these storage devices or sample holders in order to then be able to measure the corresponding samples in a fully automated manner. Usually, the samples remain in a cryogenic atmosphere from the time of their vitrification until measurement, i.e. also during shipping.

The aforementioned procedure primarily allows the investigation of static systems. That is, the structure of the samples does not change over time. In order to gain in-sight into how reactions and processes occur in proteins, various methods for time-resolved structural analysis have been developed. In the known approaches known for time-resolved analysis, the sample is usually not frozen or vitrified, although care must also be taken in this case to ensure that the samples do not dry out. Exemplarily, the "serial fixed-target method" [2, 3, 4] may be mentioned in this context, wherein several 10000 samples are placed on a special holder and, after excitation of a reaction by light or the addition of a liquid, are each measured individually and with a specific time delay. By varying the time delay between excitation and vitrification over several measurements, the dynamics of the structure can thus be determined.

However, a disadvantage of the approaches known so far is the complexity of the setups associated with these methods. A further disadvantage is that the preparation of the samples cannot be separated in time and space from the measurement at a synchrotron radiation source. That is, in the approaches known so far, the samples must be prepared just before a measurement at a synchrotron radiation source [5].

For time-resolved studies at electron microscopes, which typically use a different type of sample holder, approaches exist to start a reaction of the sample by a light pulse or the addition of a liquid and then stop it after a certain time delay by freezing or vitrification. By preparing several samples vitrified with different time delays, insights into the dynamics of the reaction can be obtained. From practice, approaches are known by which this process can be run semi-automatically or reproducibly, but only for sample holders used for measurements at electron microscopes.

Vitrifying samples for measurements at synchrotron radiation sources by means of the aforementioned devices is not possible without problems, since the respective devices are not designed for the geometry of the sample holders typically used at synchrotron radiation sources according to the SPINE standard. This is due to the fact that the tip of the SPINE sample holders is far more narrow than the sample holders for electron microscopes are, and therefore the commonly used liquid dispensers have to be aligned very precisely for applying a liquid to the samples. Typical distances between sample and liquid dispenser for SPINE sample holders are in the range of about 1 mm or less. Accordingly, the risk of the sample holder colliding with the liquid dispenser is high.

OBJECT OF THE INVENTION

It is therefore an object of the invention to provide an improved possibility for freezing or vitrifying biological samples for time-resolved measurements at synchrotron radiation sources. Preferably, it is an object of the invention to provide a corresponding facility by which biological samples held on a SPINE sample holder can be vitrified as automatically and reproducibly as possible after a reaction has been triggered in the biological sample.

DESCRIPTION OF THE INVENTION

These objects are solved by methods and an apparatus having the features of the independent claims. Advantageous embodiments and applications of the invention are the subject of the dependent claims and are explained in more detail in the following description with further reference to the figures.

According to a first independent aspect of the invention, a method is provided. Preferably, the method is for, preferably automatically, vitrifying a biological sample (e.g. a protein crystal). The process of "vitrifying", which is known per se, may preferably be understood as cooling the sample below the freezing point without (water-)crystals forming in the sample. For this, fast cooling rates (e.g. cooling rates greater than one million degrees Celsius per second) are intended, which may be realized, for example, by immersing the samples in a bath of liquid nitrogen or liquid ethane. Accordingly, the term vitrifying may preferably refer to shock freezing of the biological samples. Due to the rapid cooling (e.g. within a few milliseconds), the water molecules do not find time to form ice crystals, but they solidify and form a solid usually amorphous body, so that the vitrified samples maintain a structure as close to reality as possible.

The method according to the invention comprises positioning a sample holder with the biological sample by a transfer device in a first position, which may be referred to as "starting position" in the following for better differentiation. In this regard, it is provided that the sample holder comprises a base and a (e.g. elongated) pin, wherein the pin projects from the base along a holder axis. For example, the pin may have a first end that is attached to (e.g., inserted in) the base and a second end, opposite the first end, that is free. Thus, the sample holder may be, for example, a sample holder according to the SPINE standard. Furthermore, the biological sample is attached to the pin (e.g., by a mesh or a microscopic loop) distant from the base. Thus, the biological sample may be held on the pin (e.g., at its second end) at a predetermined distance from the base.

The method further comprises adding a liquid (e.g., water or a liquid solution of an active substance) to the biological sample in the starting position by a liquid dispenser. That is, preferably, moistening of the sample by the liquid dispenser is to be performed in the starting position. In this context, liquid dispenser may be refer as a device for controlled (e.g. dropwise) dosing of the liquid. For example, for adding the liquid, a liquid outlet (e.g., the end of a cannula) of the liquid dispenser may be positioned at a distance of a few millimeters, preferably at a distance <1 mm, from the biological sample. Advantageously, the liquid, in particular the active substance, may start a chemical and/or enzymatic reaction in the biological sample.

The method further comprises moving the sample holder with the biological sample by the transfer device along a predetermined transfer path from the first position or the starting position to a second position, which may be referred to as release position. Thus, preferably the (moistened) sample is to be transferred from the starting position to the release position by the transfer device after the liquid has been added, or a reaction has been started. Here, it is provided that the biological sample in the release position is arranged in or adjacent to a liquefied gas (e.g. liquid nitrogen or liquid ethane). Accordingly, freezing or shock freezing of the (moistened) biological sample may take place in the release position. This may be achieved, for example, by the biological sample already being surrounded by the liquefied gas in the release position or by the biological sample or sample holder being released from the transfer device in the release position and falling into the liquefied gas by gravity (i.e. under the effect of gravity). This may advantageously preserve the current state of the biological sample (e.g., a reaction intermediate formed by the addition of liquid).

The method is characterized by the fact that the transfer path is inclined with respect to the holder axis. This means that the sample holder with the biological sample is preferably moved oblique to the holder axis (e.g. with an angle of inclination between 10° and 30°). Advantageously, this ensures that the sample holder does not collide with the liquid dispenser during transfer. Advantageously, this allows the samples to be vitrified quickly, since no time needs to be spent on retracting the liquid dispenser to avoid a collision. A further advantage of the controlled movement is that a large number of samples (e.g. with different time delays and thus reaction states) can be vitrified in short time and thus a set of samples can be provided for synchrotron radiation sources, which enables time-resolved structural investigations.

According to a first aspect, the transfer path may be straight. In other words, the transfer path may preferably run straight or have a linear course.

In addition or alternatively, the transfer path may extend without a change of direction. In other words, the transfer path may preferably run along the shortest connection between the starting position and the release position.

In addition or alternatively, the movement of the sample holder with the biological sample from the starting position to the release position may comprise solely a translatory movement. In other words, the movement of the sample holder with the biological sample should preferably not include any rotational movement of the sample holder with the biological sample. In this way, a simple and fast transfer movement may be achieved in an advantageous manner.

According to a further aspect, the transfer path may be inclined with respect to the holder axis by an inclination angle, wherein the inclination angle may be an angle between 5° and 45°, preferably between 10° and 30°, particularly preferred between 10° and 20°. The inclination angle may preferably refer to the, preferably acute, angle which the holder axis of the sample holder forms with its direction of movement.

In addition or alternatively, the transfer path may be inclined with respect to the holder axis by an inclination angle, whereby the inclination angle may be greater than a threshold angle $\beta_{min}$. In other words, the transfer path may preferably run oblique to the holder axis by at least $\beta_{min}$. Preferably, this threshold angle $\beta_{min}$ is thereby determined by $\beta_{min}=\arctan((D/2-M+N)/L)$. Thereby, D denotes a lateral dimension (e.g., the diameter) of the base, M denotes a predetermined maximum distance between the liquid dispenser and the biological sample (e.g., 1 mm), N denotes a predetermined safety distance between the liquid dispenser and the pedestal, and L denotes a length of the pin. Here, M and/or N may also assume the value 0, if necessary. Advantageously, this ensures collision-free transfer of the sample holder with the biological sample.

According to a further aspect, the holder axis may be oriented along the direction of gravity in the starting position. For example, the second end of the pin of the sample holder may point substantially vertically downward and/or the sample may be arranged below the base. Advantageously, in this way, it may be achieved that the sample holder is immersed in the liquefied gas with the sample first or, if necessary, initially only a part of the pin with the sample is immersed in the liquefied gas, in order to avoid as far as possible strong turbulence in the liquefied gas during the vitrification.

According to a further aspect, the transfer path may extend in such way that the sample holder and/or the transfer device move past the liquid dispenser without collision when moving from the starting position to the release position. That is, when moving from the starting position to the release position, there should preferably be no mechanical contact between the sample holder and the liquid dispenser or the transfer device and the liquid dispenser.

According to a further aspect, a, preferably adjustable, predetermined period of time may be waited between adding the liquid in the starting position and moving the sample holder with the biological sample from the starting position to the release position. In other words, the method may comprise a, preferably adjustable, time delay between adding the liquid and starting the movement of the sample holder with the biological sample. Via the time delay or the predetermined period of time, the state in which the biological sample is finally vitrified after starting a reaction (by adding the liquid) may be adjusted in an advantageous manner. It is particularly preferred that the process is carried out for several samples with different (e.g. increasing) time delays. Advantageously, a set of samples for synchrotron radiation sources may be provided, from which knowledge about the temporal behavior of the reaction or the temporal change of the structure of the samples may be obtained.

In addition or alternatively, a position of the liquid dispenser may not be altered between adding the liquid in the starting position and moving the sample holder with the biological sample from the starting position to the release position. In other words, preferably, a position and orientation of the liquid dispenser should not be varied after the liquid has been added, at least until the sample holder with the biological sample is in the release position. In particular, preferably, there should thus be no retraction of the liquid dispenser prior to the transfer process. In an advantageous manner, this may ensure the fastest possible sample transfer after wetting. In this context, however, it should be mentioned that the liquid dispenser may in principle be configured to be movable (e.g., slidable), e.g., to facilitate removal of the vitrified samples. However, no corresponding movement of the liquid dispenser should take place during the aforementioned time period.

According to a further aspect, the method may further comprise optically exciting the biological sample in the starting position with at least one light pulse by an irradiation device. In other words, the biological sample may preferably be irradiated with a light pulse generated by an irradiation device (e.g., a laser). Thus, in addition to moistening the sample, a (e.g. chemical) reaction in the sample may be induced and/or influenced in an advantageous manner by a respective optical excitation.

According to a further aspect, the method may further comprise providing a predetermined humidity and/or temperature in an environment of the sample in the starting position by a conditioning device. Advantageously, the sample may thus be protected from drying out and/or a defined temperature may be set.

According to a further aspect, the method may further comprise releasing the sample holder with the biological sample from the transfer device in the release position by a release device of the transfer device. That is, preferably, the release device may be configured to release a positive and/or non-positive connection between the sample holder with the biological sample and the transfer device. Preferably, after releasing, the sample holder with the biological sample should thus be removable from the transfer device. In a preferred embodiment, it is provided that releasing the sample holder from the transfer device in the release position is effected by a release device of the transfer device in such a way that the sample holder may fall off the transfer device by gravity. Advantageously, this allows the sample holder with the biological sample to be released from the transfer device without the need for any external assistance.

According to a second independent aspect of the invention, a further method is provided. Preferably, also the further method is for, preferably automatically, vitrifying a biological sample (e.g., a protein crystal). As already explained above in detail in connection with the first independent aspect, also the further method according to the second independent aspect comprises positioning a sample holder with the biological sample by a transfer device in a first position, which may be referred to as "starting position". Again, the sample holder comprises a base and a (e.g., elongated) pin, wherein the pin projects from the base along a holder axis. For example, the pin may have a first end that is attached to (e.g., inserted in) the base and a second end, opposite the first end, that is free. Thus, the sample holder may be, for example, a sample holder according to the SPINE standard. Furthermore, it is envisaged that the biological sample is attached to the pin (e.g., by a mesh or a microscopic loop) distant from the base. Thus, the biological sample may be held on the pin (e.g., at its second end) at a predetermined distance from the base.

Also, the further method further comprises adding a liquid (e.g., water or an aqueous solution of an active substance) to the biological sample in the starting position by a liquid dispenser. The liquid dispenser may be configured as described above in connection with the first independent aspect.

The further method further comprises moving the sample holder with the biological sample by the transfer device along a predetermined transfer path from the first position or starting position to a second position, which may be referred to as "release position". Again, in the release position, the biological sample is provided to be located in or adjacent to a liquefied gas (e.g., liquid nitrogen or liquid ethane). Accordingly, freezing or shock freezing of the (moistened) biological sample may take place in the release position. This may be achieved, for example, by the biological sample already being surrounded by the liquefied gas in the release position or by the biological sample or sample holder being released from the transfer device in the release position and falling by gravity into the liquefied gas.

While according to the first independent aspect the transfer path is inclined with respect to the holder axis, in the alternative according to the second independent aspect it is provided that the transfer path runs along a circular arc. That is, preferably, the sample holder with the biological sample performs a partial circular motion as it moves from the staring position to the release position. For example, in a particularly preferred embodiment, the transfer path may describe, for example, a quarter-circle arc. Advantageously, this ensures that the sample holder does not collide with the liquid dispenser during transfer. Thus, in an advantageous way, the fastest possible vitrification of the samples may be achieved, since no time has to be spent on retracting the liquid dispenser. A further advantage of the aforementioned controlled movement is also that a large number of samples (e.g. with different time delays and thus reaction states) may be vitrified in a short time and thus a set of samples may be provided for synchrotron radiation sources, which enables time-resolved structural investigations.

According to a first aspect, the transfer path may run substantially along a quarter circular arc. That is, preferably, the holder axis in the release position may be oriented 90° rotated relative to the holder axis in the starting position.

In addition or alternatively, moving the sample holder with the biological sample from the starting position to the release position may comprise solely a rotational movement. In other words, moving the sample holder with the biological sample should preferably not include any translatory movement of the sample holder with the biological sample. In this way, the simplest and quickest possible transfer movement may be achieved in an advantageous manner.

According to another aspect, the holder axis may be oriented substantially perpendicular to the direction of gravity in the starting position. For example, the pin or holder axis of the sample holder may be substantially horizontal in the starting position.

According to a further aspect, the further method may further comprise, except in cases of clear incompatibility, the optional features set forth above in connection with the method according to the first independent aspect. In other words, the features described in this document in connection with the first independent aspect shall—as far as transferable—also be disclosed and claimable in connection with the second independent aspect. Correspondingly, the same applies vice versa. In particular, thus also in the further method, optically exciting the biological sample, providing a predetermined humidity and/or temperature in an environment of the sample and/or a releasing the sample holder from the transfer device in the release position may be provided.

Furthermore, the invention also relates to a vitrification apparatus, which is configured to perform one of the methods described in this document. Again, the features described in this document in connection with the methods shall also be disclosed and claimable in connection with the vitrification apparatus. Correspondingly, the same applies vice versa.

The vitrification apparatus may comprise a container for receiving the liquefied gas. For example, the container may be configured to receive liquid nitrogen, ethane and/or methane. For example, the container may be a heat-insulating tray and/or a Dewar container.

Furthermore, the vitrification apparatus may comprise a transfer device with a mount for holding the sample holder with the biological sample. The mount may be configured, for example, to fix the sample holder with the biological sample positively and/or non-positively to the transfer device. For example, the mount may comprise an electromagnet and/or a clamping device for this purpose. Furthermore, the transfer device may be configured to position the sample holder with the biological sample mounted in the mount in the starting position and to move it along the predetermined transfer path from the starting position to the release position. In addition or alternatively, the transfer device may also be configured to use the mount to position the sample holder with the biological sample in the starting position and to move it along the predetermined transfer path from the starting position to the release position. For this purpose, the transfer device may, for example, comprise (e.g., pneumatic and/or hydraulic) actuators and/or guides to enable a corresponding movement of the sample holder with the biological sample. Merely by way of example, in the case that the transfer path is linear, the movement of the sample holder with the biological sample may be carried out, for example, by a linear adjuster. In the case that the transfer path runs along a circular arc, the movement of the sample holder with the biological sample may be carried out, for example, by a servomotor.

Furthermore, the vitrification apparatus may also comprise a liquid dispenser for adding the liquid to the biological sample in the starting position. Thereby, the liquid dispenser may be configured to dispense the corresponding liquid dropwise (e.g., with droplet sizes of about 50 μm). Preferably, the liquid dispenser is configured to dispense a droplet sequence at a generation rate of 1-2 kHz, thereby advantageously generating a liquid film on the biological sample in a controlled manner. In one embodiment, the vitrification apparatus may also comprise multiple liquid dispensers for supplying the liquid to the biological sample in the starting position.

Further, the vitrification apparatus may comprise at least one of the following optional components: an irradiation device, a conditioning device, a release device, and a storage device.

The irradiation device (e.g. a laser) may be arranged to optically excite the biological sample in the starting position by at least one light pulse. Thus, the biological sample should preferably be in the beam path of the irradiation device in the starting position. Advantageously, by this, a (e.g. chemical) reaction in the sample may be stimulated and/or influenced.

The conditioning device may be configured to provide a predetermined humidity and/or temperature in an environment of the biological sample in the starting position. For example, the conditioning device may be configured to provide a water mist and/or temperature-controlled air in the environment of the biological sample in the starting position.

The release device may preferably be configured to release a positive and/or non-positive connection between the sample holder with the biological sample and the transfer device. By the release device, the sample holder with the biological sample may thus be released for removal of the sample holder from the transfer device and/or the holder.

The storage device may preferably be arranged in the container for receiving the liquefied gas. Furthermore, the storage device (e.g. in the form of a rotatable magazine) may have at least one receptacle in which the sample holder with the biological sample may be accommodated. Preferably, the at least one receptacle is configured in such a way that the sample accommodated in the at least one receptacle is not in direct contact with the storage device. In a particularly preferred embodiment, the storage device is further arranged such that, when the sample holder with the biological sample is in the release position, the at least one receptacle is arranged below the sample holder with the biological sample. In an advantageous manner, the sample holder with the biological sample may thus fall into the at least one receptacle of the storage device by gravity and by this quasi-automatically after release from the holder of the transfer device by the release device.

The aspects and features of the invention described above may be combined. Further details and advantages of the invention are described below with reference to the accompanying drawings.

FIGURE DESCRIPTION

Figure 2:
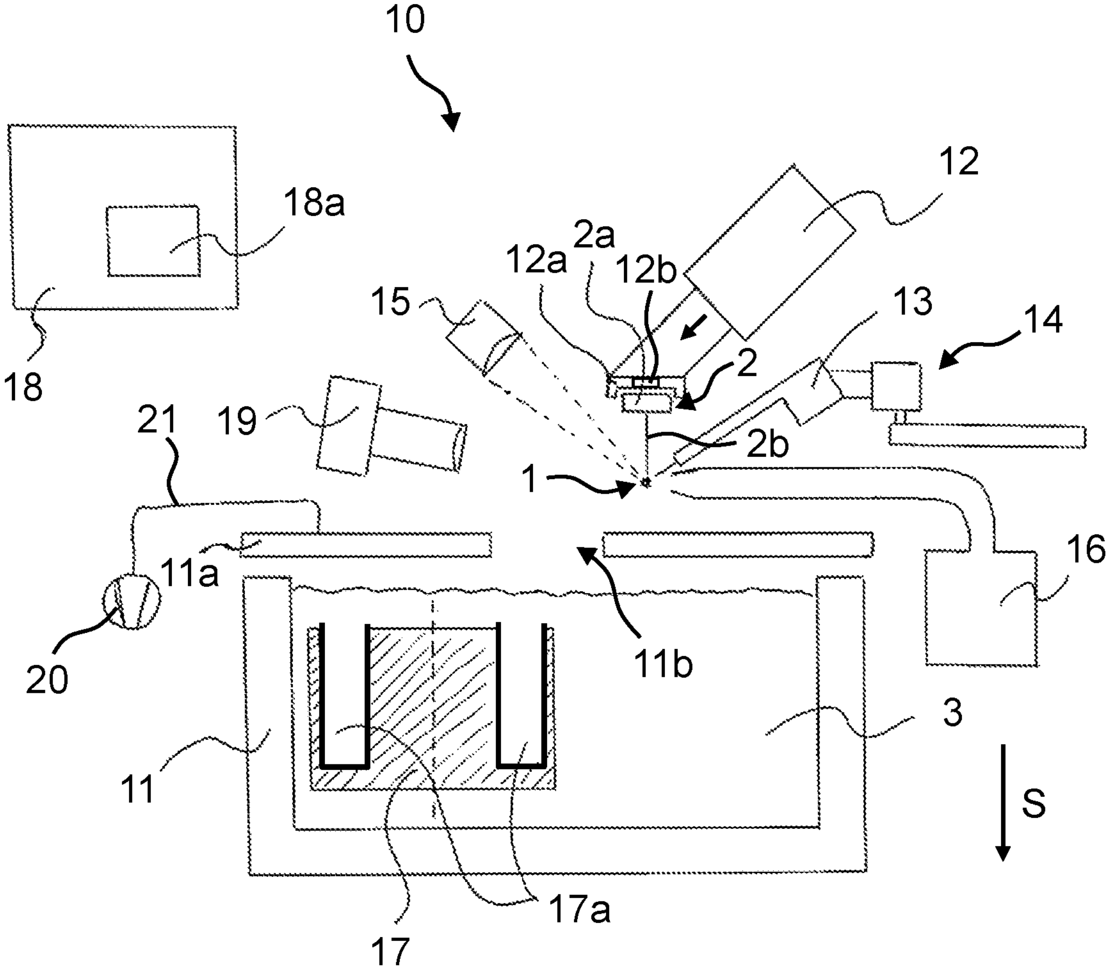
Figure 3:
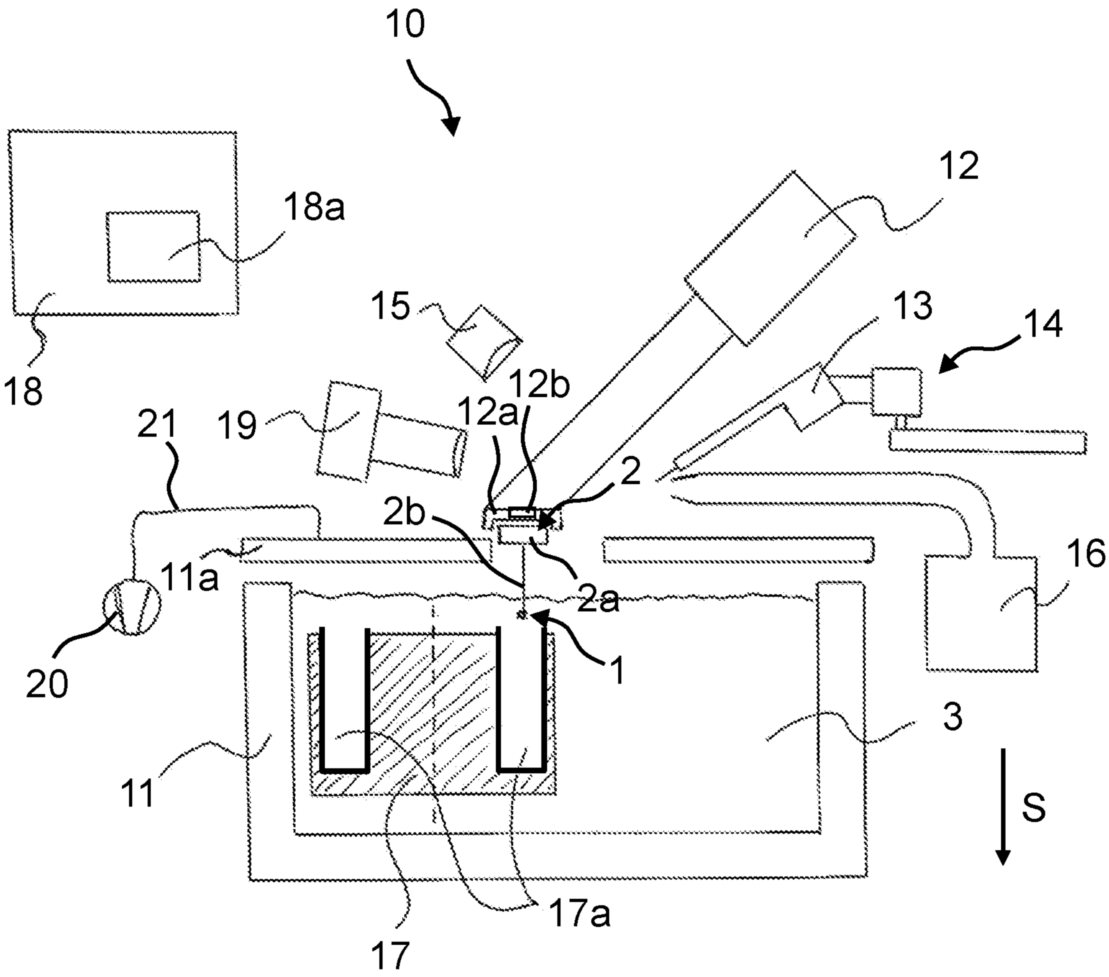
Figure 4:
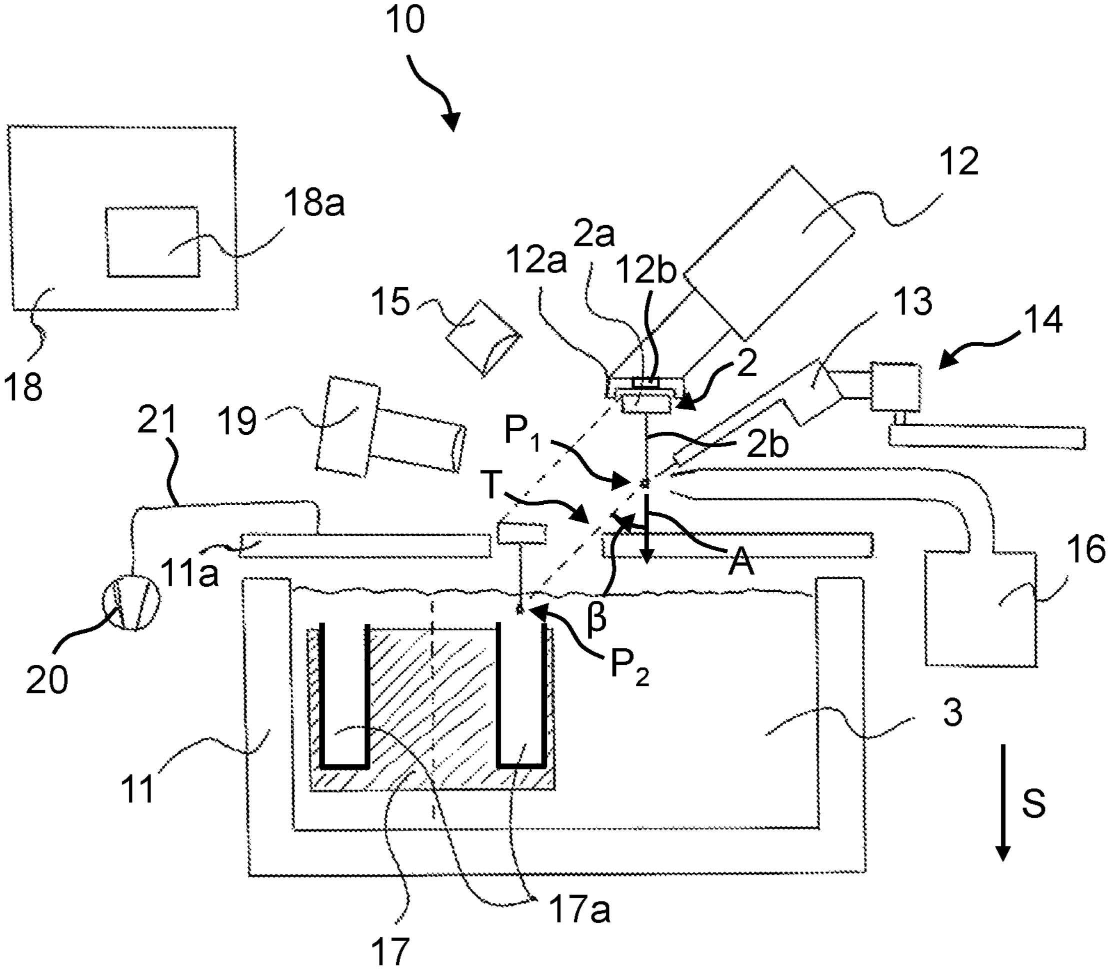
Figure 5:
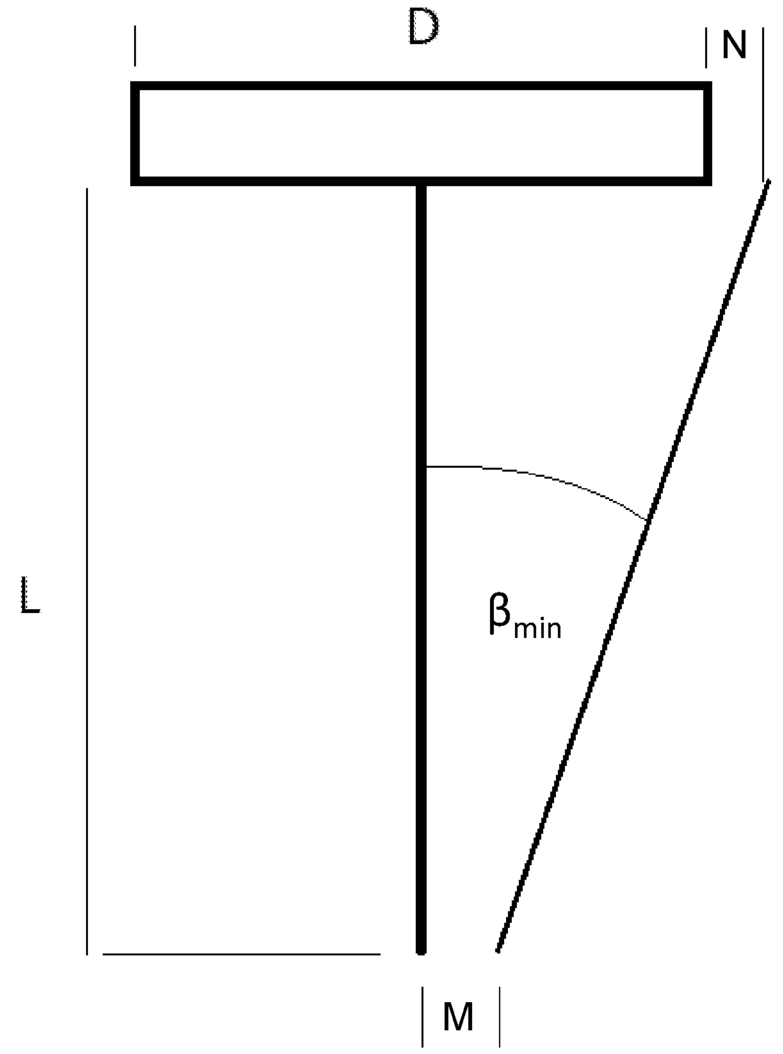

FIG. 1: A flow diagram of a method for vitrifying of a biological sample according to one embodiment;

FIG. 2: A schematic representation of a vitrification apparatus according to one embodiment, wherein the sample holder with the biological sample is in the starting position;

FIG. 3: A schematic representation of the vitrification apparatus shown in FIG. 2, with the sample holder containing the biological sample in the release position;

FIG. 4: A further schematic representation of the vitrification apparatus shown in FIGS. 2 and 3;

FIG. 5: A schematic representation of the geometric relationships between the sample holder and the liquid dispenser for determining a threshold angle for an inclination angle of the transfer path according to one embodiment; and FIG. 6: A schematic representation of a vitrification apparatus according to a further embodiment, wherein the sample holder with the biological sample is in the starting position.

Identical or functionally equivalent elements are described in all figures with the same reference signs and in some cases are not described separately.

DETAILED DESCRIPTION OF THE PREFERRED EMBODIMENT

FIG. 1 shows a flow chart of a method for vitrifying a biological sample 1. The biological sample 1 may be, for example, an organic substance such as biomolecules. In step $S_1$, a sample holder 2 with the biological sample 1 is positioned by a transfer device 12 in a first position $P_1$, referred to as starting position. In other words, preferably, the sample holder 2 with the biological sample 1 is brought into a predetermined position (=starting position N). The starting position N may thereby preferably refer to a location and/or an orientation of the sample holder 2 with the biological sample 1 in three-dimensional space. The sample holder 2 should preferably have a base 2*a* and a pin 2*b* projecting from the base 2*a* along a holder axis A. For example, the sample holder 2 may be a sample holder 2 according to the SPINE-standard. Preferably, it is provided that the biological sample 1 is attached to the pin 2*b* (e.g., by a mesh or microscopic loop) distant from the base 2*a*. For example, a distance between the biological sample 1 and a bottom of the base 2*a* oriented opposite to the pin 2*b* may be 22 mm.

In step $S_2$, a liquid (e.g. water or a liquid solution of an active substance) is added to the biological sample 1 in the starting position N by a liquid dispenser 13. Preferably, adding the liquid serves to start a, e.g. chemical and/or enzymatic reaction in the biological sample 1. The liquid dispenser 13 may be configured to add the liquid to the biological sample 1 dropwise, e.g. with an average droplet size of about 50 μm and/or a droplet generation rate of about 1-2 kHz. The liquid dispenser 13 may further be spaced a few millimeters, preferably <1 mm, from the biological sample 1 to add the liquid. Accordingly, the method may further comprise positioning the liquid dispenser 13 such that the liquid dispenser 13, in particular a liquid outlet of the liquid dispenser 13, is spaced from the biological sample 1 in the starting position $P_1$ less than 2 mm, preferably less than 1 mm.

In step $S_3$, the sample holder 2 with the biological sample 1 is moved by the transfer device 12 along a predetermined transfer path T from the first position or starting position $P_1$ to a second position $P_2$, referred to as release position. The movement of the sample holder 2 with the biological sample 1 may also be referred to as transferring. The term transfer path T may preferably denote the path of movement of the sample holder 2 with the biological sample 1 from the starting position $P_1$ to the release position $P_2$. For example, the transfer path T may be the path of movement of the center of gravity of the sample holder 2 and/or the sample 1. Here, it is envisaged that the biological sample 1 is located in or adjacent to a liquefied gas 3 in the release position $P_2$. Liquefied gas 3, which may also be referred to as liquid gas, is preferably to be understood as a gas 3 liquefied by cooling and/or compression, which remains cold and liquid at normal pressure due to the enthalpy of vaporization. For example, the liquefied gas 3 may be liquid nitrogen, liquid methane and/or liquid ethane. Depending on whether the release position $P_2$ is located in the liquefied gas 3 or adjacent thereto, vitrifying of the biological sample 1 may take place in the release position $P_2$ either immediately or after a corresponding immersion of the biological sample 1 in the liquefied gas 3 (e.g., after releasing the sample holder 2 from the transfer device 12 and a subsequently free falling into the liquefied gas 3). Advantageously, the current state of the biological sample 1 (e.g., a reaction intermediate produced by the liquid addition) may thus be preserved for subsequent investigations (e.g., at a synchrotron radiation source).

The corresponding method is characterized by the fact that the aforementioned transfer path T is inclined with respect to the holder axis A (alternative 1) or that the transfer path T runs along a circular arc (alternative 2), which will be described in more detail in connection with FIGS. 3 and 6.

Furthermore, a preferred embodiment provides that the above-described procedure is carried out for several biological samples 1 (e.g., in parallel or successively), with the respective procedures differ in a respective time delay between the adding of the liquid and the start of the movement of the sample holder 2 with the biological sample 1. By way of example only, ten biological samples 1 may thus be vitrified with ten different (e.g. increasing) time delays, in order to be able to gain knowledge in an advantageous manner about the temporal behavior of the reaction or the temporal change in the structure of the biological samples 1 by subsequent structural investigations of the biological samples 1 at a synchrotron radiation source.

FIGS. 2 to 4 show various schematic illustrations of a vitrification apparatus 10 according to one embodiment. The vitrification apparatus 10 is configured to perform one of the methods described in this document (e.g. in connection with FIG. 1).

For this purpose, the vitrification apparatus 10 may comprise a container 11 for receiving the liquefied gas 3. For example, the container 11 may be configured to receive liquid nitrogen and/or liquid methane. For example, the container 11 may be tub-shaped. The container 11 may be fillable with the liquefied gas 3 up to a given target fill level. The container 11 may have a lid 11*a* with at least one recess 11*b* (for example, a cut-out). The lid 11*a* with the with at least one recess 11*b* may close the container 11 from above, whereby access from the outside into the interior of the container 11 should preferably be possible via the at least one recess 11*b*. Preferably, the at least one recess 11*b* is configured to allow for inserting of the sample holder 2 or biological sample 1 into the interior of the container 11. The lid 11*a* may serve to thermally insulate the liquefied gas 3 received in the container 11 from the environment. That is, the lid 11*a* may reduce direct contact between the liquefied gas 3 and the ambient air. Further, the vitrification apparatus 10 may comprise a pump 20 (e.g., a diaphragm pump). The pump 20 may be used to draw (cold) gases generated above the liquefied gas 3, thereby reducing a generation of fog from residual moisture in the ambient air. For this purpose, the pump 20 may be in fluid communication, e.g. via a line connection 21 penetrating the lid 11*a*, with a region of the container 11 located between the lid 11*a* and the liquefied gas 3 or the target level.

The vitrification apparatus 10 may further comprise a transfer device 12 with a mount 12*a* for receiving the sample holder 2 with the biological sample 1. The mount 12*a* may, for example, be configured to secure the sample holder 2 with the biological sample 1 to the transfer device 12 in a form-fitting and/or force-fitting manner. For example, the mount 12*a* may comprise an electromagnet and/or a clamping device for this purpose. At least in sections, the mount 12*a* may be form-fitted to the sample holder 2. For example, an inner contour of the mount 12*a* may be formed at least in sections to match the shape of an outer contour of the base 2*a* of the sample holder 2. Furthermore, the transfer device 12 may comprise a release device 12*b*. The release device 12*b* may be configured to release a positive and/or non-positive connection between the sample holder 2 with the biological sample 1 and the transfer device 12. Via the release device 12*b*, the sample holder 2 with the biological sample 1 may thus be released from the transfer device 12 or the mount 12*a* for removal of the sample holder 2 with the biological sample 1.

The transfer device 12 may also be configured to position the sample holder 2 with the biological sample 1 received in the mount 12*a*, preferably a sample holder 2 configured according to the SPINE standard, in the starting position $P_1$ (cf. FIG. 2). In other words, the transfer device 12 may be configured to hold the sample holder 2 with the biological sample 1 at a predetermined location and/or in a predetermined orientation in three-dimensional space by the mount 12*a*. Preferably, the starting position $P_1$ is located above the container 11. Further, preferably, the holder axis A in the starting position $P_1$ is oriented along the direction of gravity S. However, the holder axis A may also be oriented obliquely to the direction of gravity S. By way of example only, the mount 12*a* may have a downward oriented contact surface against which the base 2*a* of the sample holder 2 rests in the mounted state, so that the biological sample 1, which is attached to the pin 2*b*, is arranged below the base 2*a* in the starting position $P_1$.

Further, the vitrification apparatus 10 may comprise at least one liquid dispenser 13 for adding the liquid to the biological sample 1 in the starting position N. The at least one liquid dispenser 13 may be configured to dispense the corresponding liquid dropwise (e.g., with droplet sizes of about 50 μm). The at least one liquid dispenser 13 may be configured to dispense a droplet sequence at a generation rate of 1-2 kHz, thereby advantageously generating a liquid film on the biological sample 1 in as controlled a manner as possible. For example, the at least one liquid dispenser 13 may here comprise a cannula fluidically connected to a liquid reservoir (not shown) and having an outlet opening. The outlet opening may be or may be positioned at a distance of a few millimeters, preferably at a distance <1 mm, from the biological sample 1. For this purpose, the vitrification apparatus 10 may comprise at least one adjustment device 14 (e.g., a linear adjuster) by which the at least one liquid dispenser 13 is movable. For example, the at least one liquid dispenser 13 and/or the outlet opening may be movable towards the biological sample 1 and/or retractable from the biological sample 1 by the at least one adjustment device 14. In a preferred embodiment, the at least one adjustment device 14 comprises at least two adjustment devices 14 (not separately referenced) for this purpose. For example, the at least two adjustment devices 14 may comprise a coarse adjustment device, by which the at least one liquid dispenser 13 may be moved over greater distances (e.g., in order to obtain better access for changing the sample holder 2), and a fine adjustment device, by which it is possible to position the at least one liquid dispenser 13 or the outlet opening on the biological sample 1 as precisely as possible. By supplying the liquid or wetting the biological sample 1 by the at least one liquid dispenser 13, a chemical and/or enzymatic reaction may be triggered in the biological sample 1, for example.

In order to position the at least one liquid dispenser 13 as precisely as possible on the biological sample 1, the vitrification apparatus 10 may further comprise at least one macro camera 19. Preferably, the at least one macro camera 19 comprises multiple (e.g., two) macro cameras 19, which are preferably aligned to the biological sample 1 at different viewing angles. The at least one macro camera 19 may be arranged to capture a spatial area around the biological sample 1 in the starting position $P_1$. Preferably, one of the at least one macro camera 19 is thereby arranged oriented perpendicular to a direction of movement of the at least one liquid dispenser 13. The vitrification apparatus 10 may further comprise an output device (e.g., a display screen) (not shown) on which image data captured by the at least one macro camera 19 is displayed.

Furthermore, the vitrification apparatus 10 may comprise a, preferably switchable, irradiation device 15. The irradiation device 15 (e.g., a laser) may be arranged to optically excite the biological sample 1 in the starting position $P_1$ by at least one light pulse. In other words, by the irradiation device 15, the biological sample 1 may be irradiated with a light pulse generated by an irradiation device 15. Accordingly, in the starting position $P_1$, the biological sample 1 may preferably be located in the optical path of the irradiation device 15 (indicated by the dashed line). In addition or alternatively to moistening the biological sample 1 in the starting position $P_1$, a reaction may thus also be induced and/or influenced in the biological sample 1 in an advantageous manner.

The vitrification apparatus 10 may further comprise a conditioning device 16. The conditioning device 16 may be configured to provide a predetermined humidity and/or temperature in an environment of the biological sample 1 in the starting position N. For example, the conditioning device 16 may be configured to generate a water mist and/or temperature-controlled air in the environment of the biological sample 1 in the starting position N. In other words, by the conditioning device 16, a controlled atmosphere may be provided in the vicinity of the biological sample 1. In an advantageous manner, the biological sample 1 may thereby be protected from drying out. In addition or alternatively, constant reaction conditions may also be provided in this way.

After appropriate preparation or modification of the biological sample 1 in the starting position $P_1$, it may then be preserved or vitrified for subsequent investigations (e.g. at a synchrotron radiation source). For this purpose, the transfer device 12 may be configured to move the sample holder 2 with the biological sample 1 accommodated in the mount 12*a* along the predetermined transfer path T from the starting position $P_1$ to the release position $P_2$ (cf. FIG. 2). That is, the transfer device 12 may be configured to transfer the sample holder 2 with the biological sample 1 along the predetermined transfer path T from the starting position Pito the release position $P_2$ by the mount 12*a*. In the release position $P_2$, the biological sample 1 may be arranged in the liquefied gas 3 (e.g. liquid nitrogen or liquid ethane)—as shown. Accordingly, in the release position $P_2$, vitrification or shock freezing of the biological sample 1 may occur immediately. In an alternative variant, the biological sample 1 may also initially still be arranged above the liquefied gas 3 or above the target fill level in the release position $P_2$ (not shown). Preferably, in the release position $P_2$, the biological sample 1 is arranged adjacent to the liquefied gas 3 or the target level. In other words, in the release position $P_2$, the biological sample 1 may be located in the immediate vicinity of the liquefied gas 3 or the target level, e.g., less than 1 cm away from the liquefied gas 3 or the target level. In this embodiment, vitrification of the biological sample 1 may take place after a release of the sample holder 2 with the biological sample 1 from the transfer device 12 or the mount 12*a* by the release device 12*b* and a subsequent gravity-mediated falling of the sample holder 2 with the biological sample 1 into the liquefied gas 3.

Preferably, the vitrification apparatus 10 comprises a storage device 17. The storage device 17 may be arranged in the container 11 for receiving the liquefied gas 3. The storage device 17 may, for example, be in the form of a rotatable magazine. The storage device 17 may have at least one receptacle 17*a*. Preferably, the at least one receptacle 17*a* has a plurality (for example, ten) of receptacles 17*a*. The biological sample 1 may be receivable in the at least one receptacle 17*a*. Preferably, the at least one receptacle 17*a* is thereby configured such that the biological sample 1 received in the at least one receptacle 17*a* is not in direct contact with the storage device 17. For example, the at least one receptacle 17*a* may be in the form of a cylindrical and/or vial-shaped container. Preferably, a diameter of the container is adapted to a diameter of the base 2*a* of the sample holder 2 in such a way that the base 2*a* may be accommodated in the container only partially. Further preferably, the at least one receptacle 17*a* together with the sample holder 2 with the biological sample 1 may be removed on the storage device 17. Furthermore, the storage device 17 may be arranged in such a way that, when the sample holder 2 with the biological sample 1 is in the release position $P_2$, the at least one receptacle 17*a* is arranged directly below the sample holder 2 with the biological sample 1. In an advantageous manner, the sample holder 2 with the biological sample 1 may thereby fall into the at least one receptacle 17*a* of the storage device 17 in a gravity-mediated manner and thus quasi-automatically after being released from the mount 12*a* of the transfer device 12 by the release device 12*b*. In a further variant, it may also be provided that the vitrification apparatus 10 only has a corresponding attachment point for attaching the storage device 17, without the storage device 17 itself being a mandatory component of the vitrification apparatus 10.

After the configuration of the vitrification apparatus 10 in the starting position $P_1$ (FIG. 2) and in the release position $P_2$ (FIG. 3) have been discussed above, the transfer path T and the transfer movement will be discussed again below with reference to FIG. 4. In this embodiment, it is provided that the transfer path T is inclined with respect to the holder axis A. As mentioned above, the term transfer path T shall preferably refer to the path of movement of the sample holder 2 with the biological sample 1 from the starting position $P_1$ to the release position $P_2$. For example, the transfer path T may be the path of movement of the center of gravity of the sample 1 (cf. dashed line in FIG. 4). As shown by way of example, the transfer path T may be inclined at an inclination angle β of 45° with respect to the holder axis A. Preferably, however, an angle of inclination β of between 10° and 20° is provided. Furthermore, the transfer path T in this embodiment preferably extends without a change of direction. Accordingly, the movement of the sample holder 2 with the biological sample 1 from the starting position $P_1$ to the release position $P_2$ may comprise here, by way of example, exclusively a translational movement. It is further preferred that a duration of the transfer movement is in the range of a few tenths to a hundred milliseconds (e.g. 50 ms).

For this purpose, the transfer device 12 may, for example, have (e.g., pneumatic and/or hydraulic) actuators and/or guides to enable appropriate movement of the sample holder 2 with the biological sample 1. For example, in the present embodiment, the transfer device 12 may have a (e.g., pneumatic) linear unit configured to move the mount 12*a* or the sample holder 2 with the biological sample 1 along a straight line. In this context, it should be noted that the sample holder 2 with the biological sample 1 is not necessarily a component of the vitrification apparatus 10, but the vitrification apparatus 10 is merely configured to enable a corresponding movement of the corresponding components along the transfer path T. In one variant, however, the vitrification apparatus 10 may also comprise the sample holder 2 with the biological sample 1.

Preferably, it is further provided that by the vitrification apparatus 10 a time delay between the supply of the liquid in the starting position $P_1$ and the movement of the sample holder 2 with the biological sample 1 from the starting position $P_1$ to the release position $P_2$ is adjustable. Via the aforementioned time delay, the state in which the biological sample 1 is ultimately vitrified after starting a reaction (by adding liquid) may be altered in an advantageous manner. This is particularly advantageous if the procedure is carried out for several (identical) biological samples 1 with different (e.g. increasing) time delays, in order to thereby investigate the temporal behavior of the reaction or the temporal change in the structure of the biological samples 1. To control the time delay, the vitrification apparatus 10 may comprise a control device 18. The control device 18 may be configured to operate the transfer device 12 and/or the at least one liquid dispenser 13 (e.g., with an adjustable time delay). By the control device 18, it may preferably be possible to control a time of the supply of the liquid by the at least one liquid dispenser 13 and/or a time of the start of the movement from the starting position $P_1$ to the release position $P_2$. Furthermore, the control device 18 may also be configured to operate the release device 12*b*, the irradiation device 15, the conditioning device 16 and/or the macro camera 19. In a preferred embodiment, the control device 18 further also comprises a safety device 18*a*, which is configured to block the transfer device 12 from extending during a change of the sample holder 2.

FIG. 5 shows a schematic representation of the geometric relationships between the sample holder 2 and a liquid dispenser 12 for defining a threshold angle $\beta_{min}$ for an inclination angle β of the transfer path T. As mentioned above, in one embodiment the transfer path T may run oblique to the holder axis A of the sample holder 2. In this regard, in order to advantageously avoid collisions with the liquid dispenser 12 when transferring the sample holder 2 with the biological sample 1, the transfer path T may run inclined with respect to the holder axis A by an inclination angle β that is larger than a threshold angle $\beta_{min}$. That is, the inclination angle β shall preferably have at least a value of $\beta_{min}$ here. This threshold angle $\beta_{min}$ may be given here by the relation $\beta_{min}=\arctan((D/2-M+N)/L)$. Here, D denotes a lateral dimension of the base 2*a*. For example, D may be a diameter of the base 2*a*. The lateral dimension shall preferably denote a dimension of the pedestal 2*a* in a direction perpendicular to the holder axis A. M denotes a predetermined maximum distance between the liquid dispenser 13 and the biological sample 1. For example, M may have a value of 1 mm. The predetermined maximum distance between the liquid dispenser 13 and the biological sample 1 may be given by the performance or aiming accuracy of the liquid dispenser 13. N denotes a predetermined safety distance between the liquid dispenser 13 and the base 2*a*. For example, this may be used to account for possible inaccuracies in positioning. L designates a length of the pin 2*b*. Preferably, the length of the pin is the distance between the free (second) pin end and the base 2*a*.

Figure 6:
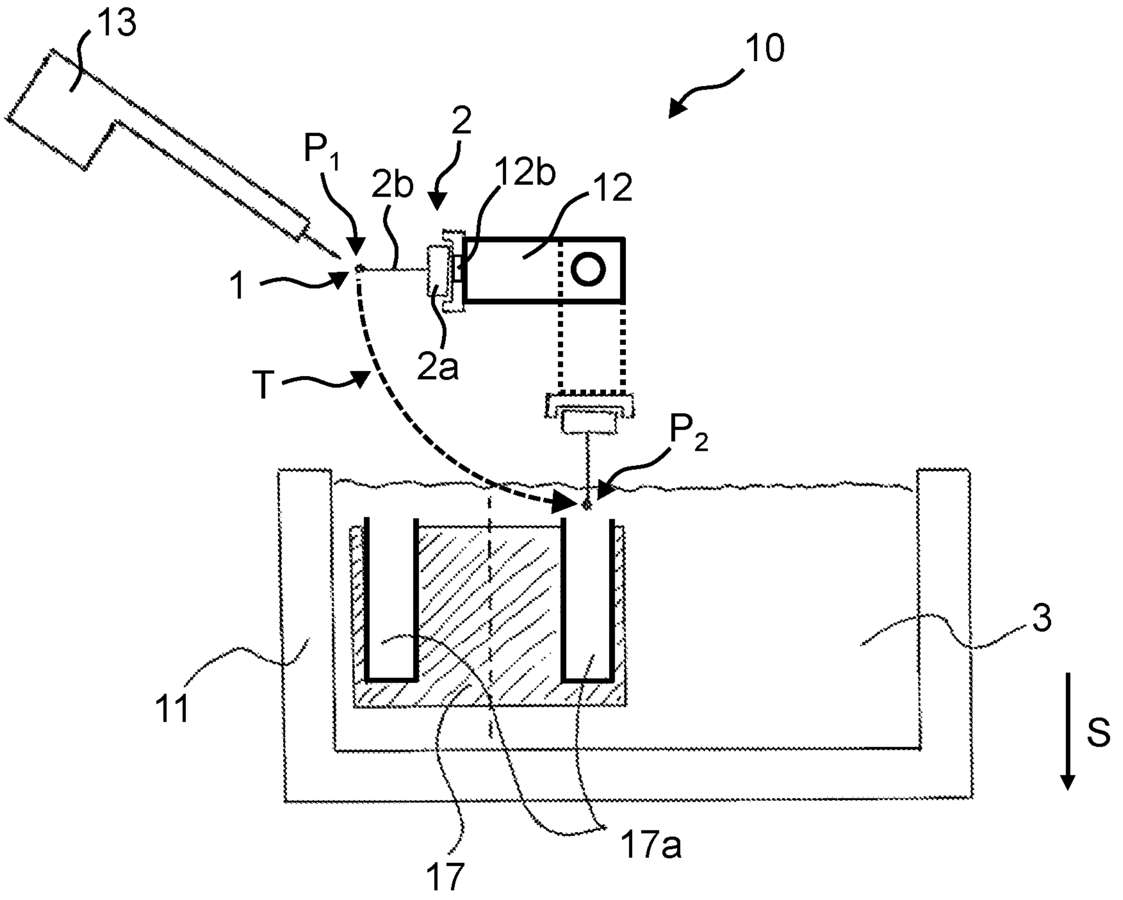

FIG. 6 shows a schematic representation of a vitrification apparatus 10 according to a further embodiment. FIG. 6 serves primarily to illustrate the alternative transfer mechanism, which is why a number of the further optional components, e.g. the irradiation device 15, the conditioning device 16, etc., have been omitted. In contrast to the embodiment described above in connection with FIGS. 2 to 5, it is provided here that the transfer path T runs along a circular arc (cf. dashed line in FIG. 6). As shown by way of example, the transfer path T may thereby run essentially along a quarter circular arc. In other words, the holder axis A in the release position $P_2$ may be oriented rotated by 90° to the holder axis A in the starting position $P_1$. Preferably, the holder axis A is oriented perpendicular to the direction of gravity S in the starting position $P_1$. However, the holder axis A may also be oriented obliquely to the direction of gravity S. Furthermore, moving the sample holder 2 with the biological sample 1 from the starting position $P_1$ to the release position $P_2$ may comprise only a rotational movement. For this purpose, the transfer device 12 may, for example, have corresponding actuators to enable a corresponding movement of the sample holder 2 with the biological sample 1. For example, in the present embodiment, the transfer device 12 may comprise a servomotor (not shown), wherein the mount 12*a* may be motion-coupled to the rotor of the servomotor, for example via a corresponding extension.

Although the invention has been described with reference to specific embodiments, it is apparent to the skilled person that various modifications may be made and equivalents may be used as substitutes without departing from the scope of the invention. Consequently, the invention is not intended to be limited to the disclosed embodiments, but is intended to encompass all embodiments that fall within the scope of the appended claims. In particular, the invention also claims protection for the subject matter and features of the dependent claims independent of the claims referenced therein.

The invention claimed is:

1. A method for vitrifying a biological sample, comprising the steps:

positioning a sample holder with the biological sample by a transfer device in a starting position, wherein the sample holder has a base and a pin projecting from the base along a holder axis, and wherein the biological sample is attached to the pin distant from the base;

adding a liquid to the biological sample in the starting position by a liquid dispenser;

moving the sample holder with the biological sample by the transfer device along a predetermined transfer path from the starting position to a release position, wherein the movement of the sample holder with the biological sample from the starting position to the release position comprises solely a translatory movement, the biological sample is located in or adjacent to a liquefied gas in the release position wherein, in the case of the arrangement adjacent to the liquefied gas, the sample holder is released from the transfer device in the release position and falls into the liquefied gas under the effect of gravity; and the transfer path is inclined with respect to the holder axis.

2. The method according to claim 1, wherein:

the transfer path is straight or extends without a change of direction.

3. The method according to claim 1, wherein the transfer path is inclined with respect to the holder axis by an inclination angle, wherein the inclination angle:

a) is an angle between 5° and 45°; or b) between 10° and 30°; or c) between 10° and 20°.

4. The method according to claim 1, wherein the transfer path is inclined with respect to the holder axis by an inclination angle, wherein the inclination angle is greater than a threshold angle, βmin, where the threshold angle is determined by $\beta min=\arctan((D/2-M+N)/L)$, where D is a lateral dimension of the base, M is a predetermined maximum distance between the liquid dispenser and the biological sample while moving the sample holder with the biological sample by the transfer device along the transfer path from the starting position to the release position, N is a predetermined safety distance between the liquid dispenser and the base, and L is a length of the pin.

5. The method according to claim 1, wherein the holder axis is oriented along the direction of gravity in the starting position.

6. The method according to claim 1, wherein the transfer path extends in such a way that the sample holder and the transfer device move past the liquid dispenser without collision when moving from the starting position to the release position.

7. The method according to claim 1, wherein between adding the liquid in the starting position and moving the sample holder with the biological sample from the starting position to the release position a predetermined period of time is waited or a position of the liquid dispenser is not altered.

8. The method according to claim 1, further comprising:

optically exciting the biological sample in the starting position with at least one light pulse by an irradiation device.

9. The method according to claim 1, further comprising:

providing a predetermined humidity or temperature in an environment of the sample in the starting position by a conditioning device.

10. The method according to claim 1, further comprising:

releasing the sample holder with the biological sample from the transfer device in the release position by a release device of the transfer device, so that the sample holder can fall off the transfer device by gravity.

11. A vitrification apparatus configured to perform a method according to claim 1, comprising:

a container for receiving a liquefied gas; and a transfer device with a mount for holding a sample holder with a base and a pin projecting from the base along a holder axis, wherein the sample holder is configured for attaching the biological sample to the pin and distant from the base and the holder axis is oriented in the starting position along the direction of gravity, wherein the transfer device is configured such that the movement of the sample holder with the biological sample from the starting position to the release position comprises solely a translatory movement and the transfer device is configured to position the sample holder with the biological sample mounted in the mount in the starting position and to move it by the mount along the predetermined transfer path from the starting position to the release position;

a liquid dispenser for adding the liquid to the biological sample in the starting position, and the transfer path is inclined with respect to the holder axis.

12. The vitrification apparatus according to claim 11, further comprising:

an irradiation device arranged to optically excite the biological sample in the starting position by at least one light pulse.

13. The vitrification apparatus according to claim 11, further comprising:

a conditioning device configured to provide a predetermined humidity or temperature in an environment of the biological sample in the starting position.

14. The vitrification apparatus according to claim 11, further comprising:

a release device by which the sample holder with the biological sample can be released from the transfer device or from the mount for a removal of the sample holder.

15. The vitrification apparatus according to claim 11, further comprising:

a storage device which is arranged in the container and which has at least one receptacle in which the sample holder with the biological sample can be accommodated, wherein the storage device is arranged in such a way that, when the sample holder with the biological sample is in the release position, the at least one receptacle is arranged below the sample holder with the biological sample.

16. A method for vitrifying a biological sample, comprising the steps:

positioning a sample holder with the biological sample by a transfer device in a starting position, wherein the sample holder has a base and a pin projecting from the base along a holder axis, and wherein the biological sample is attached to the pin distant from the base;

adding a liquid to the biological sample in the starting position by a liquid dispenser;

moving the sample holder with the biological sample by the transfer device along a predetermined transfer path from the starting position to a release position, wherein the biological sample is located in or adjacent to a liquefied gas in the release position, wherein, in the case of the arrangement adjacent to the liquefied gas, the sample holder is released from the transfer device in the release position and falls into the liquefied gas under the effect of gravity, and the transfer path runs along a circular arc, wherein the movement of the sample holder with the biological sample from the starting position to the release position comprises solely a rotational movement.

17. The method of claim 16, wherein:

the transfer path runs substantially along a quarter circular arc.

18. The method of claim 16, wherein the holder axis is oriented substantially perpendicular to the direction of gravity in the starting position.

19. The method of claim 16, wherein the transfer path extends in such a way that the sample holder and the transfer device move past the liquid dispenser without collision when moving from the starting position to the release position.

* * * * *